(12) United States Patent
Asada et al.

(10) Patent No.: US 8,022,049 B2
(45) Date of Patent: Sep. 20, 2011

(54) POLYSACCHARIDE PRODUCED BY MICROORGANISM BELONGING TO GENUS BIFIDOBACTERIUM

(75) Inventors: Masanori Asada, Osaka (JP); Mamiko Kohno, Osaka (JP); Tadashi Kanaya, Osaka (JP); Tomoe Yoshino, Osaka (JP); Youichi Matsuura, Osaka (JP); Yuzo Kawahara, Osaka (JP); Shinichi Kitamura, Sakai (JP)

(73) Assignees: Morishita Jintan Co., Ltd., Osaka (JP); IPE Inc., Osaka (JP); Osaka Prefecture University Public Corporation, Osaka (JP)

( * ) Notice: Subject to any disclaimer, the term of this patent is extended or adjusted under 35 U.S.C. 154(b) by 825 days.

(21) Appl. No.: 11/993,558

(22) PCT Filed: Jun. 23, 2006

(86) PCT No.: PCT/JP2006/313043
§ 371 (c)(1),
(2), (4) Date: Dec. 21, 2007

(87) PCT Pub. No.: WO2007/007562
PCT Pub. Date: Jan. 18, 2007

(65) Prior Publication Data
US 2010/0174063 A1 Jul. 8, 2010

(30) Foreign Application Priority Data

Jul. 8, 2005 (JP) ................................. 2005-200801

(51) Int. Cl.
*A61K 31/715* (2006.01)
*C07H 1/00* (2006.01)
*C12P 19/04* (2006.01)
*C12N 5/02* (2006.01)

(52) U.S. Cl. ....... 514/54; 536/123; 536/123.1; 536/124; 435/101; 435/383

(58) Field of Classification Search .................... 514/54; 536/123, 123.1, 124; 435/101, 383
See application file for complete search history.

(56) References Cited

U.S. PATENT DOCUMENTS 5,601,999 A 2/1997 Matsuzaki et al. ............. 435/72

FOREIGN PATENT DOCUMENTS

| EP | 0068706 A1 | 5/1983 |
|---|---|---|
| JP | 59-196099 | 7/1984 |
| JP | 01-277484 | 7/1989 |
| JP | 3-229702 | 10/1991 |
| JP | 07-070209 | 3/1995 |
| JP | 07-255465 | 9/1995 |
| JP | 7-330806 | 12/1995 |
| JP | 08-092112 | 9/1996 |
| JP | 09-241179 | 9/1997 |
| JP | 2000-247895 | 12/2000 |
| JP | 2003-073286 | 12/2003 |
| WO | 03/048343 | 6/2003 |

OTHER PUBLICATIONS

Andaloussi et al.; "Isolation and characterization of exocellular polysaccharides produced by *Bifidobacterium longum*"; Appl. Microbiol Biotechnol (1995) 43:995-1000.
English translation of *J. Appl. Glycosci*; Jul. 20, 2005, vol. 52, pp. 38; "The Structure of novel polysaccharide produced by *Bifidobacterium longum* JBL05."
International Search Report, Application No. PCT/JP2006/313043.
Hatcher et al.; "Augmentation of Macrophage Phagocytic Activity by Cell-Free Extracts of Selected Lactic Acid-Producing Bacteria"; Journal of Dairy Science, vol. 76, No. 9, 1993, pp. 2485-2492.
Hidemura et al.; "Oral Administration of *Bifidobacterium longum* Culture Condensate in a Diet-Restricted Murine Peritonitis Model Enhances Polymorphonuclear Neutrophil Recruitment into the Local Inflammatory Site"; Nutrition, vol. 19, No. 3, 2003, pp. 270-274.
Nagaoka et al.; "Structural studies on a cell wall polysaccharide from *Bifidobacterium longum* YIT4028"; Carbohydrate Research 274, 1995, pp. 245-249.
Kohno et al.; "Effects of Enteric Capsules Containing *Bifidobacteria* and Lactic Acid Bacteria on the Fecal Properties in Healthy Volunteers"; Research and Development Division, Morishita Jintan Co., Ltd., vol. 18, pp. 87-92, 2004. English language abstract.
*Bifidobacterium longum* JBL05, J. Appl. Glycosci., Jul. 20, 2005, vol. 52, p. 38, B3a-10.

*Primary Examiner* — Shaojia Anna Jiang
*Assistant Examiner* — Everett White
(74) *Attorney, Agent, or Firm* — Renner, Otto, Boisselle & Sklar, LLP (57) ABSTRACT

A polysaccharide comprising galactose, glucose, rhamnose, and pyruvic acid as constituents, wherein the galactose, glucose, and rhamnose are contained in a molar ratio of 4:2:1, and the pyruvic acid is contained in an amount of 4 to 7 wt %. The polysaccharide can be obtained by culturing *Bifidobacterium longum* JBL05 (NITE BP-82) under anaerobic conditions.

6 Claims, 3 Drawing Sheets

POLYSACCHARIDE PRODUCED BY MICROORGANISM BELONGING TO GENUS BIFIDOBACTERIUM

TECHNICAL FIELD

The present invention relates to a novel polysaccharide produced by a microorganism belonging to the genus *Bifidobacterium*, and a composition containing the same, for example, food, cosmetic, or drug.

BACKGROUND ART

Microorganisms belonging to the genus *Bifidobacterium* are one of the most dominant bacteria in the intestinal bacterial flora. The microorganisms themselves can be ingested, as in the case of lactic acid bacteria. It has been reported that ingestion of the microorganisms provides properties, for example, an action of regulating the functions of the intestines by conditioning a balance in the intestinal bacterial flora, an effect of improving the serum cholesterol level, and an immunostimulating action. There are reported agents for enhancing immune functions, among the above-described properties. Examples of the agent include an antitumor agent containing lactic acid bacteria or microorganisms belonging to the genus *Bifidobacterium* as an active component (Japanese Laid-Open Patent Publications No. 7-82158), an accelerator for production of cytokine (Japanese Laid-Open Patent Publications No. 8-92112), an agent for preventing and treating inflammatory bowel diseases containing microorganisms belonging to the genus *Lactobacillus* as an active component (Japanese Laid-Open Patent Publications No. 2003-73286), a granulocyte inducer containing cell walls and/or disrupted cell walls of microorganisms belonging to the genus *Bifidobacterium* as an active component (Japanese Laid-Open Patent Publications No. 7-330806), and a water-soluble immunostimulating substance containing microorganisms belonging to the genus *Bifidobacterium* as an active component (Japanese Laid-Open Patent Publications No. 9-241179). However, active components of all of these agents are bacteria themselves or polysaccharide fractions obtained by treatment with cell wall-digesting enzymes or ultrasonic disruption of bacteria.

On the other hand, regarding the immunostimulating action provided by an extracellular polysaccharide, it is reported as the follows: an antitumor agent containing a polysaccharide produced by *Streptococcus lactis* or *Streptococcus cremoris* as an active component (Japanese Patent No. 2678673), an antitumor activity of viscous capsular polysaccharides of *Lactococcus lactis* subsp. *cremoris* or *Lactococcus lactis* subsp. *lactis* (Japanese Laid-Open Patent Publications No. 1-277484), an anti-inflammatory agent or a bone marrow cell growth accelerator containing a polysaccharide obtained from a culture suspension of microorganisms belonging to the genus *Lactobacillus* as an active component (Japanese Laid-Open Patent Publications No. 7-70209), and a preventive effect of phosphorus-containing polysaccharides produced by *Lactobacillus delbrueckii* subsp. *bulgaricus* on autoimmune diseases (Japanese Patent No. 3017493). However, all of these reports relate to polysaccharides produced by lactic acid bacteria that have been separated from yoghurt or fermented milk.

Originally, the number of microorganisms belonging to the genus *Bifidobacterium* in the human intestinal bacterial flora is larger than that of lactic acid bacteria, and it seems that polysaccharides produced by the microorganisms belonging to the genus *Bifidobacterium* in the intestine have some biological defense functions. However, reported examples of polysaccharides produced by the microorganisms belonging to the genus *Bifidobacterium* are limited to polysaccharides containing only glucose produced by *Bifidobacterium longum* (Japanese Laid-Open Patent Publications No. 7-255465) and polysaccharides containing glucose, galactose, uronic acid, and other sugars produced by *Bifidobacterium longum* (Appl. Microbiol. Biotechnol. vol. 43, pp. 995 to 1000). Furthermore, their functions are not clear.

DISCLOSURE OF INVENTION

Thus, there has been a demand for a *Bifidobacterium*-derived polysaccharide having a novel function.

The inventors had conducted an in-depth study on microorganisms belonging to the genus *Bifidobacterium* that produces highly viscous substances in the human intestine. The inventors had found that *Bifidobacterium longum* JBL05 (NITE BP-82) produces a large amount of viscous substance in a culture suspension, that this viscous substance is a novel polysaccharide, and that this novel polysaccharide has functions such as a moisturizing action and an immunostimulating action, and thus the present invention has been achieved.

The present invention provides a novel polysaccharide, said polysaccharide contains galactose, glucose, rhamnose, and pyruvic acid as constituents, the galactose, glucose, and rhamnose are contained in a molar ratio of 4:2:1, and the pyruvic acid is contained in an amount of 4 to 7 wt %.

In one embodiment, the polysaccharide has the structure of Formula (I):

The present invention also provides a method for producing the polysaccharide, said method comprising the steps of: culturing a microorganism belonging to the genus *Bifidobacterium* having an ability to produce the polysaccharide; and collecting the polysaccharide produced by the microorganism.

In one embodiment, the microorganism is *Bifidobacterium longum* JBL05 (NITE BP-82).

The present invention also provides *Bifidobacterium longum* JBL05 (NITE BP-82).

The present invention further provides a composition that comprises the polysaccharide. In one embodiment, the composition is a food composition, a cosmetic composition, or a drug composition.

In another embodiment, the food composition or drug composition is an immunostimulator, and the cosmetic composition is a moisturizing agent.

The further present invention also provides a formulation that comprises *Bifidobacterium longum* JBL05 (NITE BP-82).

The present invention provides a novel polysaccharide having a moisturizing action and an immunostimulating action. This polysaccharide is used as raw materials of, for example, food compositions, cosmetic compositions, and drug compositions. Furthermore, *Bifidobacterium longum* JBL05 (NITE BP-82) and a culture suspension containing the microorganism is also formulated, and are used as drugs such as an immunostimulator, or foods having an immunostimulatory activity, for example. Moreover, *Bifidobacterium longum* JBL05 (NITE BP-82) and its disrupted product (suspension of disrupted cells) are also formulated, and are used as cosmetic compositions, for example.

BEST MODE FOR CARRYING OUT THE INVENTION

A polysaccharide of the present invention contains galactose, glucose, rhamnose, and pyruvic acid as constituents. The galactose, glucose, and rhamnose are contained in a molar ratio of 4:2:1, and the pyruvic acid is contained in an amount of 4 to 7 wt %. This polysaccharide has the repetitive structure represented by Formula (I) below.

The polysaccharide having such a structure can be produced by *Bifidobacterium longum* JBL05 (NITE BP-82) that has been isolated from the human bowel content.

Microorganisms used in the present invention include *Bifidobacterium longum* JBL05 (NITE BP-82), but microorganisms other than this microorganism also can be used. For example, microorganisms can be obtained by separating intestinal bacteria, selecting strains that produce capsular polysaccharides around the microorganisms, and analyzing the polysaccharides. Table 1 shows the bacteriological properties of *Bifidobacterium longum* JBL05 (NITE BP-82) obtained by this screening method.

TABLE 1

| A. Morphological properties | |
|---|---|
| (1) Shape | 0.6 to 0.8 × 1.0 to 4.0 μm, clavate, Y-shaped, and curved Gram-positive bacillus |
| (2) Motility | − |
| (3) Spore | − |
| B. Culture properties*[1] | |
| (1) Shape | Round circle, smooth both on the surface and the circumference |
| (2) Size | Diameter 0.5 to 2.5 mm |
| (3) Protrusion | Protrude in the shape of a hemisphere |
| (4) Color | Yellowish-brown or milky white |
| (5) Characteristics | Slightly viscous |
| C. Physiological properties | |
| (1) Nitrate reduction | − |
| (2) Indole production | − |
| (3) Catalase | − |
| (4) Optimum growth temperature | 37° C. |
| (5) Optimum pH | pH 6.5 to 7.0 |
| (6) Degree of anaerobicity | Obligately-anaerobic |
| (7) Gas production | − |
| (8) Sugar assimilation | |
| Arabinose | + |
| Xylose | + |
| Ribose | + |
| Glucose | + |
| Galactose | + |
| Mannose | + |
| Fructose | + |
| Saccharose | + |
| Maltose | + |
| Cellobiose | − |
| Lactose | + |
| Trehalose | − |
| Melibiose | + |
| Raffinose | + |
| Melezitose | + |
| Starch | ± |

TABLE 1-continued

| | |
|---|---|
| Glycerin | − |
| Mannitol | − |
| Sorbitol | − |
| Inositol | − |

*[1]Properties of a colony obtained by application to a BL agar medium (NISSUI PHARMACEUTICAL CO., LTD.), followed by cultivation for 48 hours at 37° C. under anaerobic conditions in a closed container containing Anaero Pack (MITSUBISHI GAS CHEMICAL COMPANY, INC.)
(+: Positive, −: Negative, ±: Slightly positive)

Based on the taxonomic characteristics of the phenotype, Bergey's Manual of Systematic Bacteriology (Vol. 2 (1984)) demonstrated that strain JBL05 is *Bifidobacterium longum*. This novel microorganism was deposited at Incorporated Administrative Agency, National Institute of Technology and Evaluation, Patent Microorganisms Depositary (NPMD) (address: 2-5-8 Kazusakamatari, Kisarazu-shi, Chiba-ken 292-0818, Japan) on Mar. 3, 2005 (originally deposited date), as *Bifidobacterium longum* JBL05 (NITE BP-82).

The polysaccharide of the present invention is obtained by culturing *Bifidobacterium longum* JBL05 (NITE BP-82) in an appropriate medium. As a medium, a medium containing a carbon source and a nitrogen source that can be used by microorganisms belonging to the genus *Bifidobacterium*, and, if necessary, cysteine hydrochloride, sodium ascorbate, and a trace amount of inorganic salts, for example, is used. In particular, a medium containing skim milk or a milk constituent is preferably used in order to produce a large amount of polysaccharide. In this case, a medium can be preferably used in which enzymatically-degraded skim milk, Cultivator (a fish extract manufactured by Yaizu Suisankagaku Industry Co., Ltd.), lactose, sodium ascorbate, and the like are contained, wherein the enzymatically-degraded skim milk is obtained by degrading skim milk with an enzyme such as protease.

If *Bifidobacterium longum* JBL05 (NITE BP-82) is cultured using this medium, at a culture temperature of 20 to 40° C. under anaerobic conditions, at a pH adjusted to 4 to 7, preferably 5 to 6, for 16 to 60 hours, with stirring or standing, then a viscous substance is produced in the culture suspension.

A polysaccharide is collected from the obtained culture suspension employing methods that are commonly used by those skilled in the art in order to collect a target substance from a culture suspension, and the method include heating, enzyme treatment, centrifugation, and filtration. For example, a culture suspension containing a viscous substance (polysaccharide) and bacteria is centrifuged, and the bacteria are removed as a precipitate. If the viscosity of the culture suspension is high, the bacteria can be removed by, for example, diluting the culture suspension with water, and then centrifuging the resultant. Then, an appropriate organic solvent is added to the obtained supernatant to precipitate proteins, and the precipitate is removed by centrifugation or the like. Then, a polysaccharide is precipitated by further adding an organic solvent to the supernatant, and the polysaccharide is collected by centrifugation or the like. More specifically, a crude polysaccharide is obtained by adding ethanol at a final concentration of 20 volume % to the supernatant from which the bacteria have been removed, removing a precipitation containing protein by centrifugation, further adding ethanol at a final concentration of 50 volume % thereto, and then collecting a precipitation by centrifugation.

Alternatively, it is also possible to employ methods for collecting a polysaccharide by combining an organic solvent and cations. For example, it is possible to employ a collection methods similar to those using a monovalent cation and an organic solvent, those using a bivalent cation and an organic solvent (Japanese Laid-Open Patent Publications No. 58-5301), or those using a trivalent cation and an organic solvent (Japanese Laid-Open Patent Publications No. 59-196099), for example. Cations are preferably used in order to improve the collection rate of the polysaccharide. As the monovalent cation, a sodium ion, a potassium ion, and the like are used. As the bivalent cation, a magnesium ion, a calcium ion, and the like are used. As the trivalent cation, an aluminum ion, and the like are used. A larger amount of the polysaccharide can be collected by adding these cations together with an organic solvent such as ethanol to a viscous solution containing the polysaccharide. It is possible to improve the collection rate of polysaccharides by using bivalent or trivalent cations than using monovalent cations.

A polysaccharide can be purified from the obtained crude polysaccharide employing methods that are commonly used by those skilled in the art, for example, a method using, alone or in combination, fractionation with an ion exchange resin or fractionation by gel filtration. There is no specific limitation on a method using an ion exchange resin. For example, a method is employed in which a polysaccharide is adsorbed to an anion exchange resin (for example, product name: DEAE Sephadex A-50 (Pharmacia Corporation) etc.), eluted with gradient of sodium chloride, and then subjected to gel filtration using, for example, a product named TOYOPEARL HW65S (Tosoh Corporation). It is also possible to measure the molecular weight in purification by gel filtration.

The structure of the polysaccharide can be determined using a following method. Saccharides (monosaccharides) constituting the polysaccharide are determined by acid hydrolyzing the purified polysaccharide with an acid such as a formic acid, a dilute hydrochloric acid, or a trifluoroacetic acid, and then analyzing this hydrolysate by HPLC. Then, the composition of the constituent saccharides (the ratio between the constituent saccharides) is determined by acetylating the acid hydrolysate using a commonly used method, and then analyzing the resultant by gas chromatography (GC analysis). Furthermore, the binding state for constituents of the polysaccharide is determined by, for example, methylating the acid hydrolysate using a commonly used method, and then analyzing the resultant by GC-MS (mass). Moreover, an NMR analysis reveals the binding mode of the monosaccharides, and also detects the presence of acetyl groups. The pyruvic acid bonded to the polysaccharide can be qualitatively and quantitatively determined by measuring the reduction of pyruvic acid into lactic acid with lactate dehydrogenase in the presence of NADH.

The polysaccharide produced by *Bifidobacterium longum* JBL05 (NITE BP-82) has the following characteristics.

(1) The polysaccharide contains galactose, glucose, rhamnose, and pyruvic acid as constituents, and the galactose, glucose, and rhamnose are contained in a molar ratio of 4:2:1 in the polysaccharide.

(2) The content of pyruvic acid in the polysaccharide is 4 to 7 wt %.

(3) The molecular weight measured by gel filtration with TOYOPEARL HW65S is approximately 200000 to 2500000.

(4) The specific rotation is approximately +130°.

(5) The polysaccharide contains acetyl groups.

(6) The polysaccharide has the repetitive structure represented by Formula (I) below.

(I)

It should be noted that the molecular weight of the polysaccharide of the present invention varies depending on culture conditions and collection/purification conditions. The molecular weight can be adjusted through culture conditions and the other conditions.

The obtained polysaccharide has an excellent immunostimulatory activity and moisturizing ability. Thus, the polysaccharide can be used as compositions such as food compositions, drug compositions, and cosmetic compositions. Examples of the drug compositions include quasi drug compositions and hygiene products such as transdermal patches, wound protecting agents, and first-aid adhesive tapes, which contain the polysaccharide of the present invention.

Furthermore, *Bifidobacterium longum* JBL05 (NITE BP-82) of the present invention and a culture suspension containing this microorganism also can be formulated and used. When this formulation is delivered into the intestine, the microorganism produces the polysaccharide of the present invention, and thus this formulation can be used as, for example, drugs such as an immunostimulator or foods having an immunostimulatory activity.

EXAMPLES

Hereinafter, the present invention shall be described by way of examples, but the present invention is not limited to these examples.

Example 1

Isolation of Microorganisms (Preparation of Medium)

As a medium for isolation of Bifidobacteria, a BL agar medium (NISSUI PHARMACEUTICAL CO., LTD) and a BS agar medium were used. The BL agar medium was sterilized in an autoclave at 115° C. for 20 minutes, 5% equine blood was added thereto under sterile conditions, the resultant was poured into a petri dish, and thus the BL agar medium was used as a plate medium. The BS agar medium was prepared in the following manner. First, an additive solution for a BS agar medium was prepared in a total amount of 100 ml by dissolving 30 g of sodium propionate, 100 mg of paromomycin sulfate, 400 mg of neomycin sulfate, and 6 g of lithium chloride in purified water. Then, 50 ml of the additive solution for a BS agar medium was added to 1000 ml of a BL agar medium to give a BS agar medium. The BS agar medium was poured into a petri dish and used as a plate medium.

(Screening of Microorganisms)

Human feces were suspended in sterile water, the resultant was placed on the BL agar medium and the BS agar medium, and the cultivation was performed under anaerobic conditions at 37° C. for 48 hours. The colony properties of bacteria grown on the plates and the bacteria form of Gram-stained samples were observed, and colonies that seemed to be bifidobacteria were separated into two BL agar media. The colonies on one medium were cultured under anaerobic conditions at 37° C. for 48 hours, and the colonies on the other medium were cultured under aerobic conditions at 37° C. for 48 hours. Of the colonies grown under anaerobic conditions, colonies (microorganisms) producing a viscous substance were isolated. The physiological and morphological characteristics of the obtained microorganisms were as described above, and thus the microorganisms were identified as *Bifidobacterium longum* JBL05 (NITE BP-82).

Example 2

Structural Analysis of the Polysaccharide (Preparation of Medium)

Pancreatin (Amano Enzyme Inc.) and silicon were added at final concentrations of 0.36 wt % and 0.01 wt % respectively, to a 9 wt % skim milk liquid. Then, this liquid was adjusted to pH 8 with 10N NaOH, and allowed to react at 55° C. for four hours, and thus enzymatically-degraded skim milk was obtained. Cultivator (a fish extract manufactured by Yaizu Suisankagaku Industry Co., Ltd.), lactose, and sodium ascorbate were added to the enzymatically-degraded skim milk at final concentrations of 3.0 wt % of Cultivator, 2.5 wt % of lactose, and 0.2 wt % of sodium ascorbate respectively, the mixture was sterilized in an autoclave at 121° C. for 15 minutes, and the resultant was used as a liquid medium.

(Purification of the Polysaccharide)

*Bifidobacterium longum* JBL05 (NITE BP-82) precultured using the prepared liquid medium was inoculated at a concentration of 1% (v/v) in the same liquid medium, and subjected to stationary culture under anaerobic conditions at 37° C. for 40 hours to produce a viscous substance. The bacteria were removed by centrifugation from the obtained culture suspension, then ethanol was added at a final concentration of 20% to the supernatant, and the resultant was allowed to stand at 4° C. overnight. Then, a precipitation containing protein was removed by centrifugation, ethanol was added at a final concentration of 50% to the supernatant, and the resultant was allowed to stand at 4° C. overnight. Then, a precipitation was collected by centrifugation to give crude polysaccharide fractions. The fractions were lyophilized and stored.

The crude polysaccharide fractions were further fractionated using a column filled with DEAE Sephadex A-50, and eluted with 0.07M to 0.5M NaCl to give purified polysaccharide fractions.

(Measurement of Molecular Weight)

When the purified polysaccharide fractions were subjected to gel filtration using a column filled with TOYOPEARL HW65S, the molecular weight of the polysaccharide was approximately 800000. It should be noted that the molecular weight varies depending on culture conditions, collection conditions, and purification conditions. By repeating this experiment for several times, polysaccharides having molecular weights of approximately 200000 to 2500000 were obtained. Accordingly, it seems that the molecular weight can be adjusted through, for example, culture conditions, collection conditions, and purification conditions.

(Measurement of Specific Rotation)

The specific rotation of the polysaccharide measured using a DIP-360 digital polarimeter (JASCO Corporation) was approximately +130°.

(Analysis of Constituents)

Next, the obtained polysaccharide was hydrolyzed by adding formic acid. After the hydrolysate liquid was dried under reduced pressure, the resultant was hydrolyzed by adding trifluoroacetic acid to give a hydrolysate. An HPLC analysis using an ION-300 column (TOKYO CHEMICAL INDUSTRY CO., LTD.) showed that this polysaccharide was constituted by galactose, glucose, rhamnose, and pyruvic acid.

The hydrolysate was reduced with sodium borohydride using a commonly used method. The resultant was acetylated by adding acetic anhydride and pyridine, and then analyzed by a GC analysis using an R-225 column (J&W Scientific). As a result, it was shown that the molar ratio of galactose, glucose, and rhamnose constituting the polysaccharide was 4:2:1.

When lactate dehydrogenase was added on the hydrolysate in the presence of NADH, lactic acid was produced. Thus, it was confirmed that pyruvic acid was present in the polysaccharide fractions. Furthermore, the content of pyruvic acid in the polysaccharide was 4 to 7 wt %.

(Structural Analysis)

In order to clarify the binding mode of constituents of the polysaccharide, methylation was performed for analysis. The hydrolysate was methylated using a commonly used method. The methylated monosaccharides were analyzed by a GC-MS (mass) analysis. As a result, methylated saccharides, that is, 1,5-di-O-acetyl-2,3,4,6-tetra-O-methyl-glucitol,
1,5-di-O-acetyl-2,3,4,6-tetra-O-methyl-galactitol,
1,3,4,5-tetra-O-acetyl-2,6-di-O-methyl-rhamnitol,
1,3,5-tri-O-acetyl-2,4,6-tri-O-methyl-galactitol,
1,4,5-tri-O-acetyl-2,3,6-tri-O-methyl-glucitol,
1,4,5-tri-O-acetyl-2,3,6-tri-O-methyl-galactitol, and
1,4,5,6-tetra-O-acetyl-2,3-di-O-methyl-galactitol were obtained.

The binding state of the constituents was examined by NMR analysis. The data showed that the polysaccharide of the present invention has Structure I below (repetitive structure).

Herein, acetyl groups were detected in the NMR analysis.

Example 3

Production of the Polysaccharide by Cultivation

Sodium ascorbate was added at a final concentration of 0.2 wt % to the enzymatically-degraded skim milk prepared in Example 2. The resultant was sterilized in an autoclave at 121° C. for 15 minutes, and thus a liquid medium was prepared. The culture suspension of *Bifidobacterium longum* JBL05 (NITE BP-82) precultured in the same liquid medium was inoculated at a concentration of 1% (v/v) in the thus prepared liquid medium, and the cultivation was performed with slightly stirring, at a pH adjusted to 6.0 at 37° C. for 40 hours, under anaerobic conditions. In order to control pH, 10N NaOH was used. It should be noted that a case where stationary cultivation under anaerobic conditions was performed is taken as a comparative example.

Figure 1:
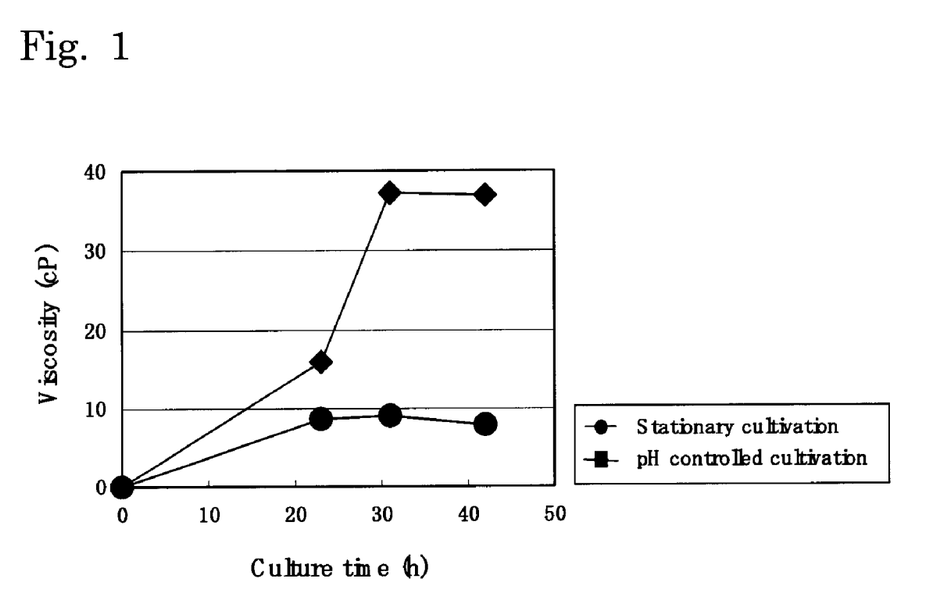
FIG. 1 is a graph illustrating the relationship between the culture time of *Bifidobacterium longum* JBL05 (NITE BP-82) and the viscosity of a culture suspension.

The relationship between the culture time and the viscosity of a culture suspension is shown in FIG. 1. The viscosity rapidly increased after 20 hours, and the polysaccharide of the present invention was efficiently produced, in a case where cultivation was performed while controlling pH, compared to a case where stationary cultivation under anaerobic conditions was performed. The viscosity was measured with a TVB-10 viscometer (TOKI SANGYO CO., LTD.) and a rotor THM1 at 15° C. at a rotation rate of 50 rpm.

Example 4

Immunostimulatory Macrophage Activating Action of the Crude Polysaccharide Fractions The immunostimulating action of the crude polysaccharide fractions prepared in Example 2 was measured in the following manner. First, a 12-week old ddY male mouse (Kiwa Laboratory Animals Co., Ltd.) was injected intraperitoneally with 2 ml of 4% (w/v) TGC medium (NISSUI PHARMACEUTICAL CO., LTD). Four days later, the abdominal cavity was washed with 12 ml of cold PBS to collect the washings. The washings were centrifuged at 10000 rpm at 4° C. for 10 minutes, and thus the supernatant was removed to give peritoneal exudate cells. The cells were suspended in an RPMI1640 medium (SIGMA-ALDRICH) containing 10% FCS (Invitrogen Japan K.K.), penicillin G, and streptomycin. The suspension was plated in a 96-well plate at a density of $5 \times 10^5$ cells/well, and cultured in the presence of 5% $CO_2$ at 37° C. At one hour after starting the cultivation, the medium was removed. Then, the cells were added to 200 μl of RPMI1640 media respectively containing 0 μg/ml, 3 μg/ml, 10 μg/ml, 30 μg/ml, and 100 μg/ml of the crude polysaccharide fractions obtained in Example 2, and (I)

cultured in the presence of 5% $CO_2$ at 37° C. for four hours or 20 hours. The culture supernatant after cultivation for four hours was used for measuring TNF-α concentration described later as an indicator of macrophage activation, and the culture supernatant after cultivation for 20 hours was used for measuring nitrite concentration described later.

The TNF-α concentration was measured in the following manner using TNF-α sensitive mouse fibroblasts (L929 cell, DAINIPPON PHARMACEUTICAL CO., LTD.). The L929 cells were plated in each well of a 96-well plate at a density of $4.0 \times 10^4$ cells/well, and cultured in the presence of 5% $CO_2$ at 37° C. for five hours. After the cultivation, the medium was removed. Then, 50 µl of RPMI1640 medium containing 1.5 µg/ml of actinomycin D was added to each well, and followed by 100 µl of the culture supernatant after cultivation for four hours. Herein, as the TNF-α standard, instead of the culture supernatant, a solution in which TNF-α (SIGMA-ALDRICH) was dissolved in RPMI1640 media at various concentrations was added at a ratio of 100 µl/well. Then, the cells were cultured in the presence of 5% $CO_2$ at 37° C. for 20 hours, 3-(4,5-dimethyl-2-thiazolyl)-2,5-diphenyl-2H tetrazolium bromide (Wako Pure Chemical Industries, Ltd.) was added thereto at a final concentration of 0.5 mg/ml, and the resultant was cultured in the presence of 5% $CO_2$ at 37° C. for four hours. Subsequently, the medium was removed, and 100 µl of isopropanol containing a 0.04N hydrochloric acid was added thereto. After formazan produced was dissolved with shaking for approximately ten minutes, the absorbance at 562 nm (reference wavelength: 660 nm) was measured. The TNF-α concentration was calculated using a calibration curve obtained from the TNF-α standard. As a test for significant difference, the Dunnett's multiple comparison test was performed at significance levels of $p<0.05$ and $p<0.01$. The results are shown in FIG. 2.

The nitrite concentration was measured by placing 50 µl of the culture supernatant after cultivation for 20 hours into each well of a 96-well plate, adding 50 µl of Griess reagent to each well, allowing to react in a dark place at room temperature for ten minutes, and then measuring the absorbance at 562 nm (reference wavelength: 660 nm). The calibration curve was obtained by measuring the absorbance as described above, except that a solution in which sodium nitrite (Wako Pure Chemical Industries, Ltd.) was dissolved in RPMI1640 media at various concentrations was used instead of the culture supernatant. The nitrite concentration was calculated using this calibration curve. As a test for significant difference, the Dunnett's multiple comparison test was performed at a significance level of $p<0.01$. The results are shown in FIG. 3.

Figure 2:
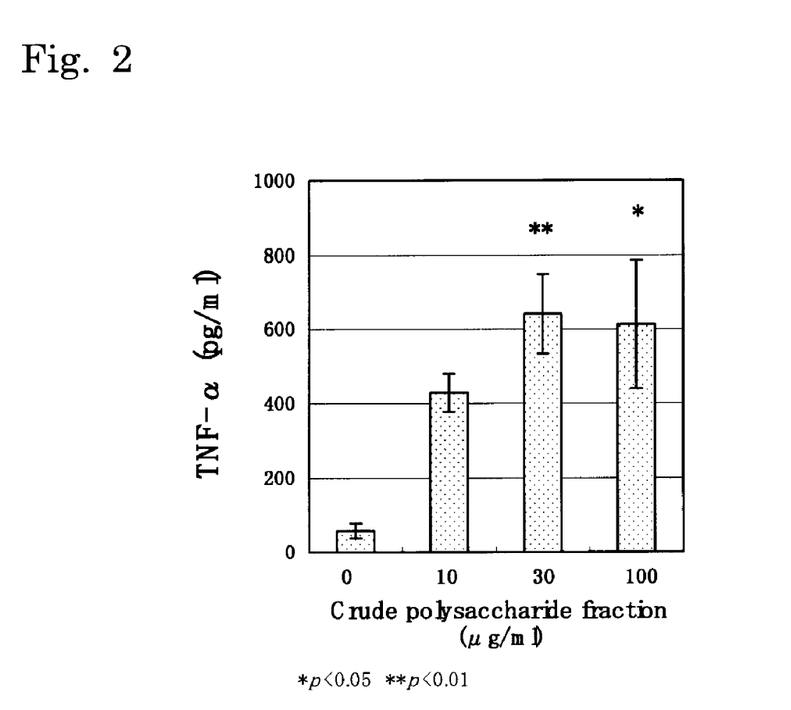
FIG. 2 is a graph illustrating an effect of a polysaccharide of the present invention on acceleration of TNF-α production.
Figure 3:
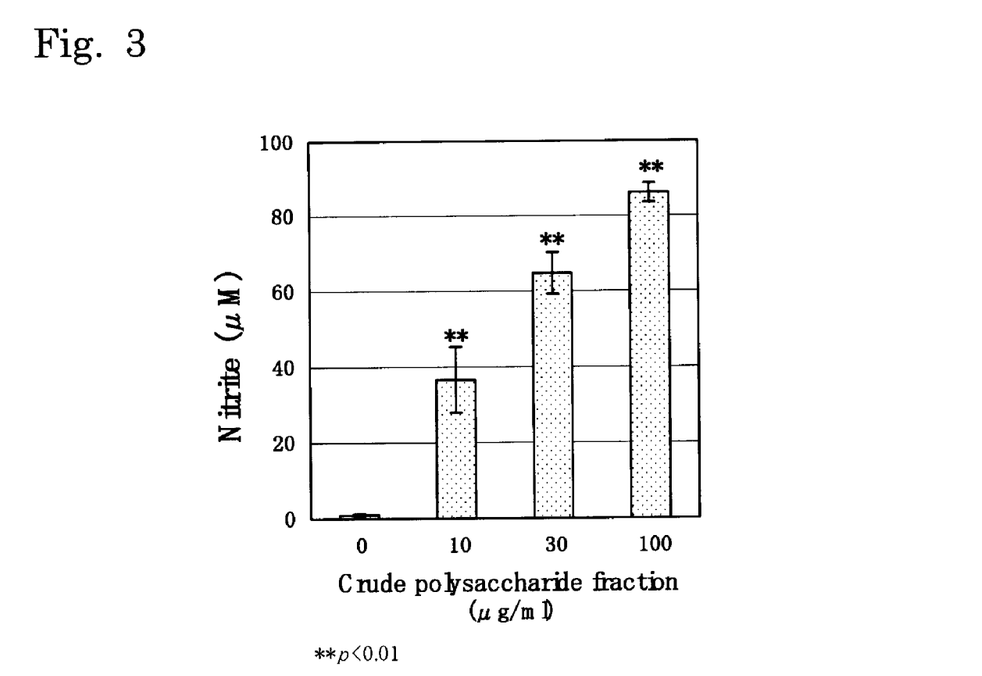
FIG. 3 is a graph illustrating an effect of the polysaccharide of the present invention on acceleration of nitrite production.

As shown in FIGS. 2 and 3, a macrophage activating action was confirmed in the crude polysaccharide fractions obtained in Example 2.

Example 5

Figure 4:
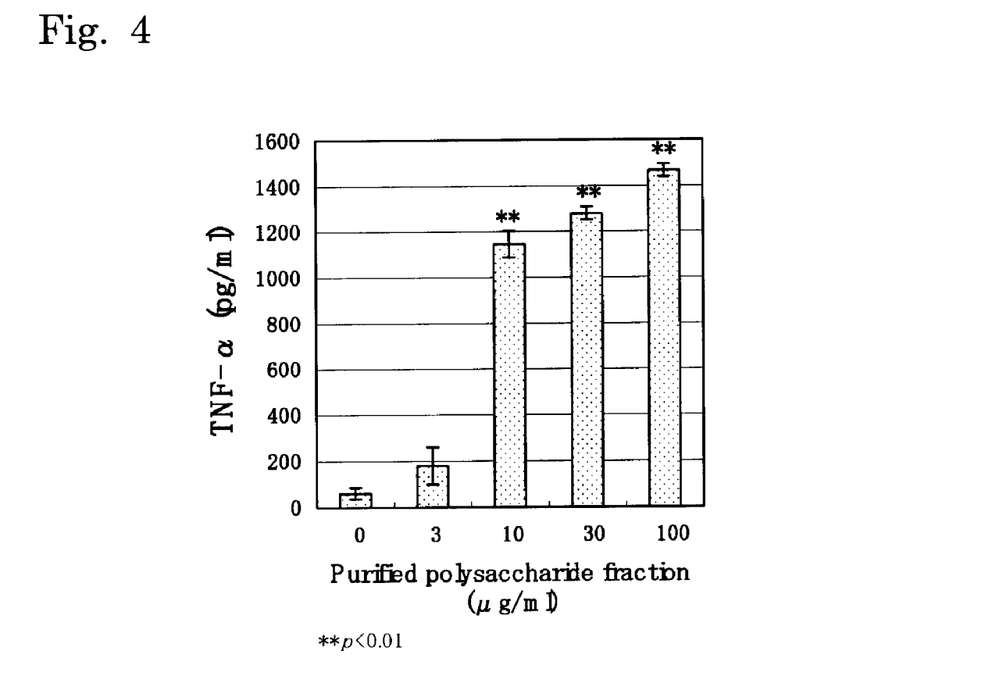
FIG. 4 is a graph illustrating an effect of the polysaccharide of the present invention on acceleration of TNF-α production.
Figure 5:
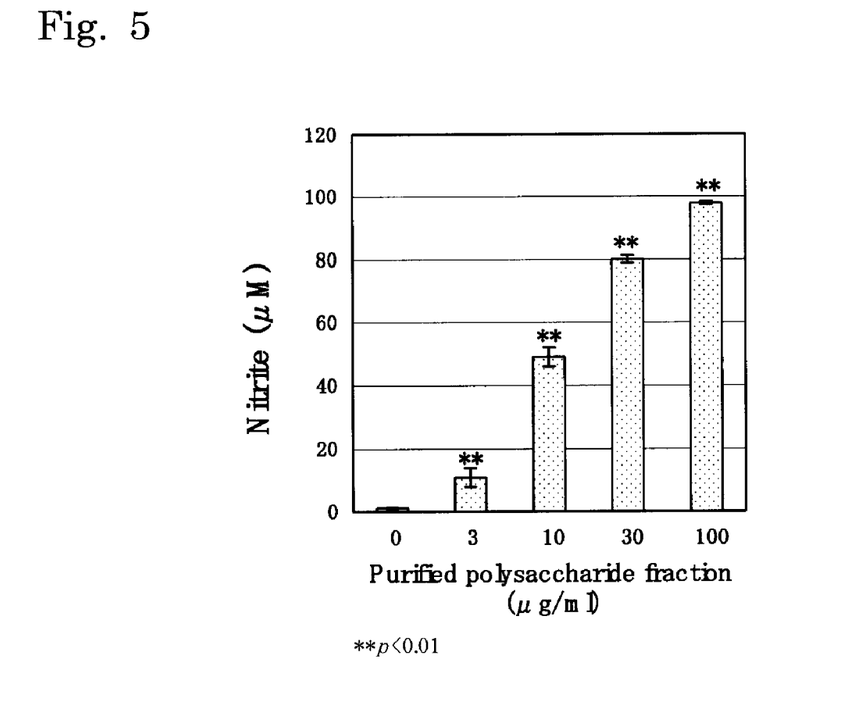
FIG. 5 is a graph illustrating an effect of the polysaccharide of the present invention on acceleration of nitrite production.

Immunostimulatory Macrophage Activating Action of the Purified Polysaccharide Fractions The TNF-α concentration and the nitrite concentration were measured as in Example 4, except that a lyophilized product of the purified polysaccharide fractions purified using the column in Example 2 was used instead of a lyophilized product of the crude polysaccharide fractions. As a result, a macrophage activating action was confirmed also in the purified polysaccharide fractions. The results are shown in FIGS. 4 and 5.

Example 6

Moisturizing Action of the Polysaccharide

Figure 6:
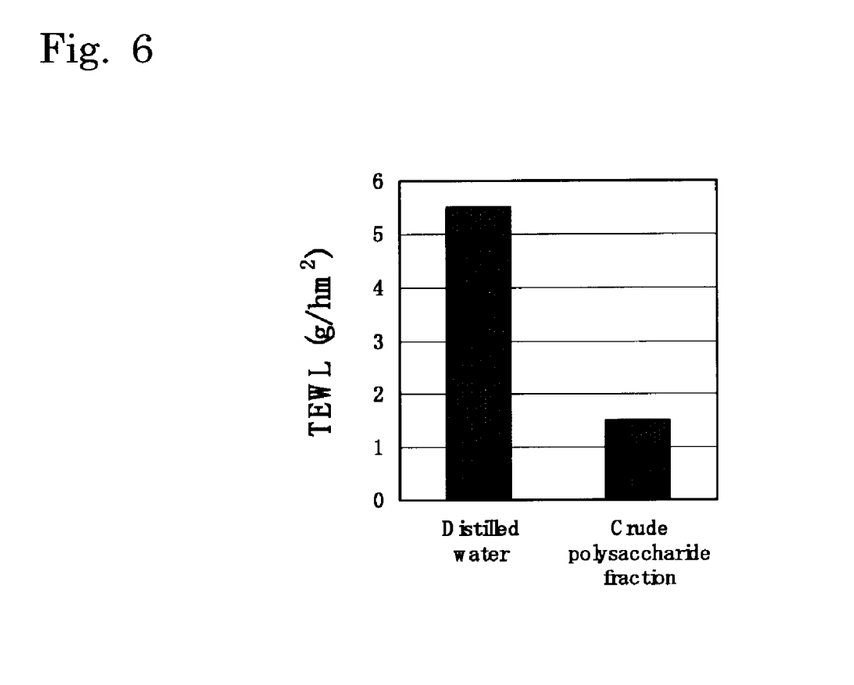
FIG. 6 is a graph illustrating a moisturizing effect of the polysaccharide of the present invention.

The lyophilized crude polysaccharide fractions prepared in Example 2 were adjusted to a concentration of 1 mg/ml of water, and the moisturizing ability thereof was confirmed based on a change in the amount of transepidermal water loss from a portion on the inner side in the upper arm of 10 women in their 20's. The test portions were marked with 2×2 cm marks at intervals of 2 cm, and the transepidermal water loss (TEWL) before sample application was measured. Then, each of 20 µl of the crude polysaccharide fractions and 20 µl of distilled water serving as control was spread with a glass rod, and the TEWL was measured at 45, 90, 150, and 210 minutes later. The measurement was performed using an apparatus (mobile Tewameter MSC100) for measuring the water loss. The amounts of water loss after 210 minutes are shown in FIG. 6. The water loss in the crude polysaccharide fractions was smaller than that of the distilled water, and thus a moisturizing effect of the crude polysaccharide fractions was confirmed.

Industrial Applicability

The polysaccharide of the present invention is a novel polysaccharide having a moisturizing action and an immunostimulating action. This polysaccharide is produced by *Bifidobacterium longum* that has been isolated from microorganisms living in the human intestine. The polysaccharide is industrially useful as raw materials of, for example, food compositions, cosmetic compositions, and drug compositions.

The invention claimed is:

1. An isolated and purified polysaccharide comprising galactose, glucose, rhamnose, and pyruvic acid as constituents,
   wherein the galactose, glucose, and rhamnose are contained in a molar ratio of 4:2:1, and
   the pyruvic acid is bonded to one or more of the galactose, glucose, or rhamnose and is contained in an amount of 4 to 7 wt %,
   wherein the polysaccharide comprising the galactose, glucose and rhamnose have the structure of Formula (I):

2. A method for producing the polysaccharide of claim 1, comprising the steps of:
   culturing a microorganism belonging to the genus *Bifidobacterium* having an ability to produce the polysaccharide; and
   collecting the polysaccharide produced by the microorganism.

3. The method of claim 2, wherein the microorganism is *Bifidobacterium longum* JBL05 (NITE BP-82).

4. A composition comprising the polysaccharide of claim 1, wherein the composition is a food composition, a cosmetic composition, or a drug composition.

5. The composition of claim 4, wherein the food composition or drug composition is an immunostimulator.

6. The composition of claim 4, wherein the cosmetic composition is a moisturizing agent.

* * * * *